US006953436B2

(12) United States Patent
Watrous et al.

(10) Patent No.: US 6,953,436 B2
(45) Date of Patent: Oct. 11, 2005

(54) MULTI-MODAL CARDIAC DIAGNOSTIC DECISION SUPPORT SYSTEM AND METHOD

(75) Inventors: Raymond Watrous, Belle Mead, NJ (US); Nathaniel Reichek, Fort Salonga, NY (US)

(73) Assignee: Zargis Medical Corp., Princeton, NJ (US)

( * ) Notice: Subject to any disclaimer, the term of this patent is extended or adjusted under 35 U.S.C. 154(b) by 102 days.

(21) Appl. No.: 10/242,394

(22) Filed: Sep. 12, 2002

(65) Prior Publication Data

US 2003/0093003 A1 May 15, 2003

Related U.S. Application Data

(63) Continuation of application No. 09/670,284, filed on Sep. 25, 2000, now Pat. No. 6,572,560.
(60) Provisional application No. 60/156,601, filed on Sep. 29, 1999, and provisional application No. 60/156,725, filed on Sep. 30, 1999.

(51) Int. Cl.$^7$ ................................................. A61B 7/00
(52) U.S. Cl. ........................ 600/528; 600/586; 128/925
(58) Field of Search ................................. 600/508, 513, 600/528, 580; 128/906, 920, 923, 925

(56) References Cited

U.S. PATENT DOCUMENTS

| 5,638,823 | A |   | 6/1997 | Akay et al. ................. 128/691 |
| 5,730,142 | A |   | 3/1998 | Sun et al. .................... 128/705 |
| 6,383,135 | B1 | * | 5/2002 | Chikovani et al. .......... 600/300 |
| 6,572,560 | B1 | * | 6/2003 | Watrous et al. ............. 600/528 |

FOREIGN PATENT DOCUMENTS

WO  WO 92/03094  3/1992

OTHER PUBLICATIONS

Barschdorff et al., "Automatic Phonocardiogram Signal Analysis in Infants Based on Wavelet Transforms and Artificial Neural Networks", Computers in Cardiology, 1995, Vienna Austria, Sep. 10–13, 1995, pp. 753–756.

Huiying et al., "A Heart Sound Feature Extraction Algorithm Based on Wavelet Decomposition and Reconstruction", Proc. Of the 20$^{th}$ Ann. Int'l. Conf. Of the IEEE Engineering in Medicine and Biology Society, Hong Kong China, Oct. 29–Nov. 1, 1998, vol. 20, No. 3, 1998, pp. 1539–1542.

Wu et al., "Computer–aided Analysis and Classification of Heart Sounds Based on Neural Networks and Time Analysis", 1995 Intl. Conf. On Acoustics, Speech and Signal Processing, Conf. Proceedings, vol. 5, 1995, pp 3455–3458.

Edwards et al., "Neural Network and Conventional Classifiers to Distinguish Between First and Second Heart Sounds", IEEE Colloquium on Artificial Intelligence Methods for Biomedical Data Processing, London, UK, Apr. 26, 1996, pp. 1–3.

\* cited by examiner

Primary Examiner—Kennedy Schaetzle
Assistant Examiner—Kristen Mullen
(74) Attorney, Agent, or Firm—RatnerPrestia (57) ABSTRACT

A method for extracting and evaluating features from cardiac acoustic signals includes the steps of obtaining a cardiac acoustic signal, extracting physiologically significant features from the cardiac acoustic signal using a neural network, analyzing the cardiac acoustic signal with a wavelist decomposition to extract time-frequency information, and identifying basic heart sounds using neutral networks applied to the extracted time-frequency information. A method for determining a status of heart murmurs includes the steps of obtaining a cardiac acoustic signal, detecting a murmur, if any, from the cardiac acoustic signal, and determining whether the murmur is one of functional and pathological based upon expert rules.

21 Claims, 4 Drawing Sheets

MULTI-MODAL CARDIAC DIAGNOSTIC DECISION SUPPORT SYSTEM AND METHOD

CROSS-REFERENCE TO RELATED APPLICATIONS

This is a continuation application of U.S. patent application Ser. No. 09/670,284, filed on Sep. 25, 2000 now U.S. Pat. No. 6,572,560, which claims priority to provisional application Ser. No. 60/156,601, filed on Sep. 29, 1999, which is incorporated by reference herein. In addition, provisional application Ser. No. 60/156,725, entitled "Handheld Sensor for Acoustic Data Acquisition", filed on Sep. 30, 1999, and U.S. patent application Ser. No. 09/670,053, filed Sep. 25, 2000, entitled "Handheld Sensor for Acoustic Data Acquisition", 2000, entitled "Handheld Sensor for Acoustic Data Acquisition", claiming the benefit of the provisional application, Ser. No. 60/156,725, are incorporated by reference herein.

BACKGROUND

1. Technical Field

The present invention relates generally to systems and methods for cardiac evaluation and, in particular, to a multi-modal cardiac diagnostic decision support system and method.

2. Background Description

In the context of the rapidly increasing cost of health care, the role of the primary care physician as a gatekeeper to the resources of the medical system is critical. The challenge in using health care resources in a cost-effective manner is especially acute in the area of heart sounds and murmurs evaluation.

A brief description of the conventional method for auscultation of the heart will now be given. The heart is listened to using a stethoscope. The primary heart sounds with reference to the sys/diastolic phase of the heart are identified. It is then determined whether there are any abnormal heart sounds present, such as murmurs and/or clicks. The relative loudness, duration, intensity pattern, spectral quality and time sequence of the heart sounds are assessed. The heart sounds are interpreted in terms of the physiological model of the action of the heart muscle, valves and chambers. A hypothesis is then developed about any possible disease states based on the acoustic evidence and knowledge of the patient's medical history. Possible diagnoses are differentiated by varying the placement of the microphone, the patient's posture, or by having the patient execute different maneuvers that accentuate or diminish certain heart sounds. The accumulated evidence is evaluated for the presence of heart disease. It is then decided whether to refer the patient for diagnostic imaging, particularly ultrasound.

A description of some of the many disadvantages of conventional auscultation of the heart will now be given. Auscultation of the heart is a difficult task, for many reasons. The stethoscope itself transfers only a small fraction of the acoustic signal at the chest surface to the listener's ears, and filters the cardiac acoustic signal in the process.

Much of the signal energy in many heart sounds is below the threshold of human hearing, and this situation only tends to worsen with increased age of the listener. Auscultation also relies on correctly determining the correspondence of the primary heart sounds with the systolic and diastolic phase of the heart, which is made more difficult when the systolic and diastolic intervals are more equal, typically at elevated heart rates. Auscultation also relies on detecting the correct sequence of brief events that are closely spaced in time, something that is difficult for human listeners.

Learning auscultation is also difficult because diagnostic instructional manuals rely on subjective descriptions of heart sounds, which require much practice to appreciate.

Furthermore, the practice and teaching of the clinical skill of auscultation of the heart has declined among physicians. Recent tests have demonstrated that physicians can identify reliably only a small number of standard heart sounds and murmurs, as described by Burdick et al., in "Physical Diagnosis Skills of Physicians in Training: A Focused Assessment", Acad. Emerg. Med., 2(7), pp. 622–29, July 1995; Mangione et al., in "Cardiac Auscultatory Skills of Internal Medicine and Family Practice Trainees: A Comparison of Diagnostic Proficiency", Journal of the American Medical Association, 278(9), pp. 717–22, September 1997; Gracely et al., in The Teaching and Practice of Cardiac Auscultation During Internal Medicine and Cardiology Training: A Nationwide Survey", Annals of Internal Medicine, 119(1), pp. 47–54, July 1997. Consequently, serious heart murmurs in many patients go undetected by physicians.

Furthermore, the decline in auscultation skills has led to an over-reliance on echocardiography, resulting in a large number of unnecessary and expensive diagnostic studies. As a result, reimbursement for echocardiography has recently come under scrutiny by Medicare.

Accordingly, it would be desirable and highly advantageous to have multi-modal cardiac diagnostic decision support system and method capable of aiding in auscultation of the heart.

SUMMARY OF THE INVENTION

The present invention is directed to a multi-modal cardiac diagnostic decision support system and method. The invention may be used to aid a physician in performing the following tasks: detect valvular heart diseases that might otherwise go undiagnosed; discriminate pathological from innocent heart murmurs, to make a better decision about referring a patient for an echocardiography study; and rationalize, and document the basis for, the referral decision.

The invention allows physicians to provide better health care to their patients at a lower cost, detect otherwise undiagnosed heart disease, save the health care system the costs of unnecessary echocardiography referrals, and facilitate reimbursement for well-justified referrals.

According to a first aspect of the invention, there is provided a method for extracting features from cardiac acoustic signals. A cardiac acoustic signal is obtained. Physiologically significant features are extracted from the cardiac acoustic signal, using a neural network.

According to a second aspect of the invention, the physiologically significant features correspond to at least one of basic heart sounds and components of the basic heart sounds.

According to a third aspect of the invention, there is provided a method for evaluating cardiac acoustic signals. A cardiac acoustic signal is obtained. The cardiac acoustic signal is analyzed with a wavelet decomposition to extract time-frequency information. Basic heart sounds are identified using neural networks applied to the extracted time-frequency information.

According to a fourth aspect of the invention, there is provided a method for determining cardiac event sequences from cardiac acoustic signals. A cardiac acoustic signal is obtained. A sequence of features extracted from the cardiac acoustic signal are processed by a probabilistic finite-state automation to determine a most probable sequence of cardiac events given the cardiac acoustic signal.

According to a fifth aspect of the invention, the probabilistic finite-state automation is a hidden markov model.

According to a sixth aspect of the invention, there is provided a method for extracting clinical findings from cardiac acoustic signals. A cardiac acoustic signal is obtained. The cardiac acoustic signal is processed to determine a most probable sequence of cardiac events given the cardiac acoustic signal. The clinical findings are extracted from the sequence of cardiac events.

According to a seventh aspect of the invention, the method further includes the step of determining whether to refer the patient for echocardiography, based upon the extracted clinical findings.

According to an eighth aspect of the invention, the method further includes the step of determining whether to refer the patient for further treatment by a cardiac specialist, based upon the extracted clinical findings.

According to a ninth aspect of the invention, the clinical findings correspond to findings which are typically derived from auscultation of a heart.

According to a tenth aspect of the invention, the clinical findings correspond to basic heart sounds and murmurs.

According to an eleventh aspect of the invention, the clinical findings include at least one of present intensity, intensity profile, duration, time-alignment, and sequence and spectral quality features.

According to a twelfth aspect of the invention, there is provided a method for determining the presence of cardiac diseases. A cardiac acoustic signal of a patient is obtained. The cardiac acoustic signal is processed to find evidence of cardiac diseases. Data corresponding to a medical record of the patient is received. A diagnostic recommendation corresponding to a probability of the cardiac diseases being present in the patient is provided, based upon an analysis of the evidence and data using Bayesian networks.

According to a thirteenth aspect of the invention, the method further includes the step of determining whether to refer the patient for echocardiography, based upon the diagnostic recommendation.

According to a fourteenth aspect of the invention, the method further includes the step of determining whether to refer the patient for further treatment by a cardiac specialist, based upon the diagnostic recommendation.

According to a fifteenth aspect of the invention, there is provided a method for determining a status of heart murmurs. A cardiac acoustic signal is obtained. A murmur, if any, is detected from the cardiac acoustic signal. It is then determined whether the murmur is one of functional and pathological, based upon expert rules.

These and other aspects, features and advantages of the present invention will become apparent from the following detailed description of preferred embodiments, which is to be read in connection with the accompanying drawings.

DETAILED DESCRIPTION OF PREFERRED EMBODIMENTS

The present invention is directed to a multi-modal cardiac diagnostic decision support system and method. It is to be understood that the present invention may be implemented in various forms of hardware, software, firmware, special purpose processors, or a combination thereof. Preferably, the present invention is implemented in software as a program tangibly embodied on a program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the program (or a combination thereof) which is executed via the operating system. In addition, various other peripheral devices may be connected to the computer platform such as an additional data storage device and a printing device.

It is to be further understood that, because some of the constituent system components and method steps depicted in the accompanying figures are preferably implemented in software, the actual connections between the system components (or the process steps) may differ depending upon the manner in which the present invention is programmed.

Figure 1:
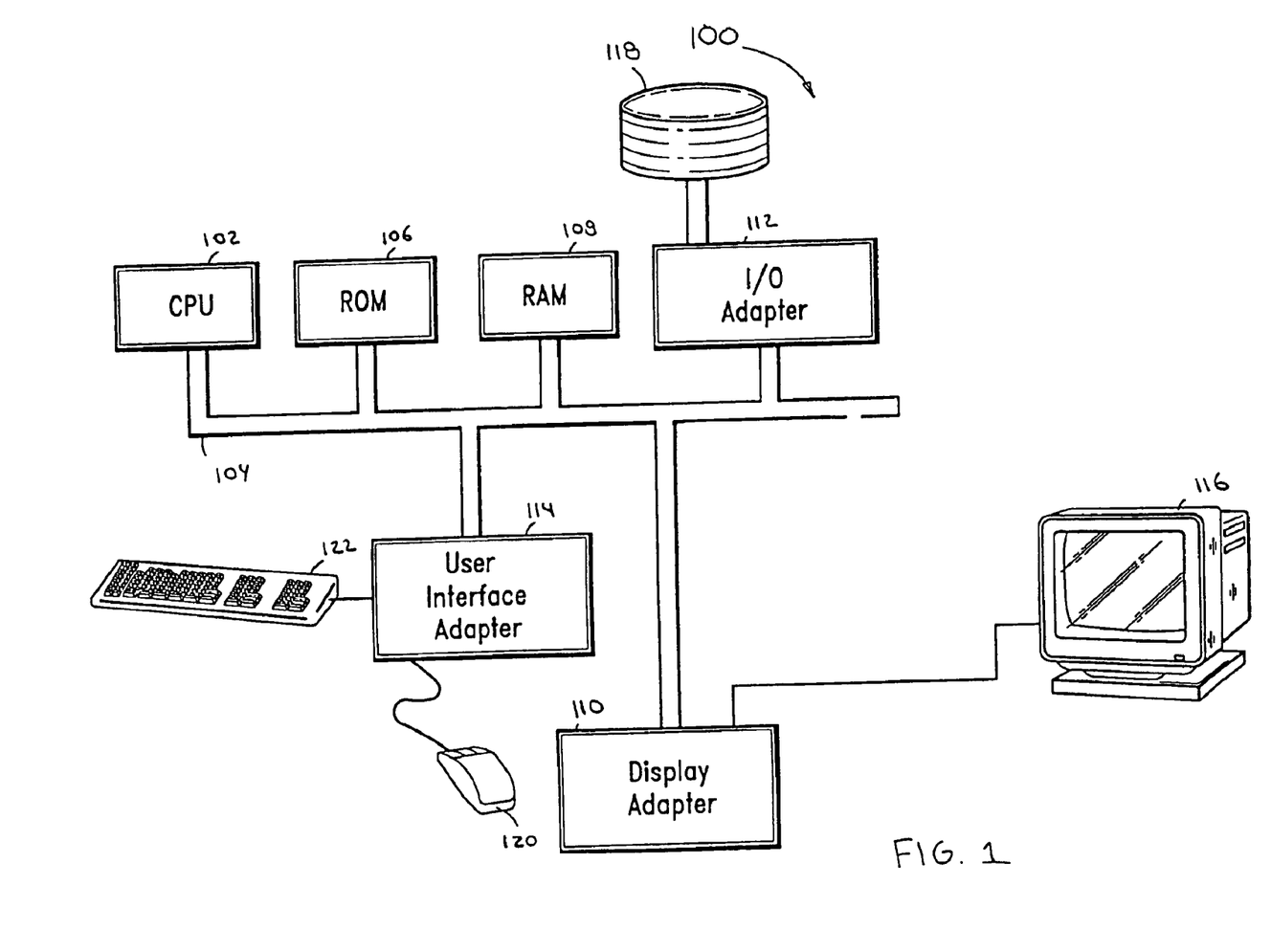
FIG. 1 is a block diagram of a computer processing system to which the present invention may be applied according to an embodiment of the present invention.

FIG. 1 is a block diagram of a computer processing system 100 to which the present invention may be applied according to an embodiment of the present invention. The system 100 includes at least one processor (hereinafter processor) 102 operatively coupled to other components via a system bus 104. A read only memory (ROM) 106, a random access memory (RAM) 108, a display adapter 110, an I/O adapter 112, and a user interface adapter 114 are operatively coupled to system bus 104.

A display device 116 is operatively coupled to system bus 104 by display adapter 110. A disk storage device (e.g., a magnetic or optical disk storage device) 118 is operatively coupled to system bus 104 by I/O adapter 112.

A mouse 120 and keyboard 124 are operatively coupled to system bus 104 by user interface adapter 114. The mouse 120 and keyboard 124 are used to input and output information to and from system 100.

A general description of the present invention will now be provided to introduce the reader to the concepts of the invention. Subsequently, more detailed descriptions of various aspects of the invention will be provided.

The invention acquires cardiac acoustic signals from the chest surface, along with optional synchronizing electrocardiogram and respiration signals. Moreover, user-provided information about the location of the acoustic sensor on the chest surface, postural information and any associated diagnostic maneuvers such as Valsalva are also acquired. The invention analyses these signals, extracts clinical findings, and generates an estimate of the probability of each of several heart diseases consistent with the clinical findings derived from the cardiac acoustic signal and patient medical record data. Based on these analyses, the invention provides diagnostic decision support to the primary care physician in deciding whether to refer the patient for further diagnostic tests such as, for example, ultrasound.

The invention provides documentation in the form of an annotated set of signals, which can be used to rationalize the referral decision. The invention also supports interaction with the user that provides an explanation for the clinical findings and diagnostic recommendation. The acquired signals, extracted features, interpretation and diagnostic results are archived for future reference, and can be made available electronically for data transfer, or for generation of printed reports. An interface to hospital medical information systems for patient data transfer and telemedical applications is included. These functions may be embodied in a lightweight, handheld, signal acquisition unit and a portable analysis and display unit or in more stationary configurations, depending on the particular implementation of the invention.

Various detailed descriptions of some of the elements of the invention will now be given.

The first such element to be described is the sensor. The signal of interest is the cardiac acoustic waveform recorded on the chest surface. Preferably, the signal is recorded using an appropriate sensor having a high signal to noise ratio (SNR), good immunity to ambient noise and motion artifact, and excellent low-frequency response, to as low as 1 Hz. The surface cardiac acoustic signal is preamplified, and digitized for signal processing and interpretation.

One sensor for this purpose utilizes a fluid interface between the sensing element (a piezoelectric accelerometer) and the chest surface to achieve good impedance matching and much improved SNR. This sensor is described by: Padmanabhan et al., in "Accelerometer Type Cardiac Transducer for Detection of Low-level Heart Sounds", IEEE Transactions on Biomedical Engineering, 40(1), pp. 21–28, January 1993. Of course, the invention is not limited to the preceding sensor and, thus, other sensors may be employed to record the cardiac acoustic waveform which maintain the spirit and scope of the invention.

The next element of the invention which will now be described is signal processing. The acquired cardiac acoustic signal is filtered using standard methods to remove motion artifact and high frequency noise. The filtering is designed to preserve signal information at very low frequencies.

The filtered signal is analyzed using a wavelet decomposition in order to extract time-frequency information. The kernel function of the wavelet decomposition is not critical to the invention. The wavelet decomposition is scaled to compensate for variations in amplitude.

A set of cardiac acoustic features is extracted from the wavelet representation using adaptive neural networks. Features are employed corresponding to basic heart sounds such as, for example, S1, S2, murmur, and ejection click. These feature detectors are trained from data using labeled examples. The feature detectors operate continuously on the wavelet decomposition to produce a stream of feature data.

The extracted features are interpreted or parsed with reference to a state-transition model of the heart. The state machine can be probabilistic, such as, for example, a hidden Markov model. Of course, other techniques and/or state transition models may be employed to interpret or parse the extracted features, while maintaining the spirit and scope of the invention.

The output of the state transition model allows determination of the cardiac phase of the signal, and subsequent identification of heart murmurs as systolic or diastolic. Other features, such as, for example, ejection clicks, M1, T1, A2 and P2 are identified and sequenced using the model.

The duration of any heart murmurs present is quantified relative to the systolic/diastolic interval, and the murmurs are labeled with reference to the phase as early-, mid-, late- or pan-systolic or diastolic. According to an illustrative embodiment of the invention, the murmur intensity is scaled by a psychoacoustic measure and graded I through VI. Of course, other measures and/or gradings may be used.

The clinical findings derived by signal processing are provided as input to the signal classification module.

The following element of the invention which will now be described is the user interface (acoustic sensor). The position of the acoustic sensor on the chest surface is an important parameter in auscultation.

The sensor position can be inferred with respect to a standard site sequence protocol, guided by the signal interpretation system, confirmed by the user, input by the user using a keyboard, mouse, or position indicator located on the acoustic sensor, or measured with reference to a standard location by a position sensor.

The patient's posture is also an important parameter of auscultation that can be provided by the user, along with any dynamic auscultation maneuvers associated with the signals being acquired at the time.

Another element of the invention which will now be described is the diagnostic decision support. The clinical findings derived by processing the cardiac acoustic signal are provided, along with available relevant patient medical record data, as inputs to a probabilistic reasoning network that is used to compute an estimate of the indication of need for echocardiography referral. The probabilistic reasoning network also estimates the posterior probabilities of cardiac diseases. The output of the probabilistic reasoning network is presented to the user as referral recommendation probability along with a rank-ordered list of the most probable cardiac diseases.

The probabilistic network can also be used to generate explanations to the user at various levels of detail in support of the diagnostic and referral recommendations.

A description of various extensions and alternatives will now be given with respect to the sensors employed by the invention, as well as applications of the invention.

The surface electrocardiogram can optionally be recorded to provide a reference signal for synchronizing the recorded acoustic signal. The recorded ECG need only comprise a single channel, requiring a single electrode and electrical reference.

A respiration signal can also be optionally recorded in order to provide information about the respiratory activity of the patient for use in the interpretation of the cardiac acoustic signal. The respiratory signal can be obtained from, for example, impedance respiration or nasal thermistor sensors.

A pulse oximetry signal can also be optionally recorded to provide information about the cardiac activity of the patient for use in the interpretation of the cardiac acoustic signal. The pulse oximetry signal can be obtained from, for example, a photoplethysmographic sensor, typically applied to the finger tip.

A pressure sensor can also be optionally incorporated with the acoustic sensor to measure the application pressure of the acoustic sensor to the chest surface. This sensor can be used to detect instances where the application pressure is too low or too high; if the pressure is too low, the acquired signal amplitude will be low, whereas too high a pressure will create a diaphragm of the surface skin and result in modified spectral properties.

A position sensor can also be optionally incorporated with the acoustic sensor to measure the position of the acoustic sensor with respect to some reference point. Alternatively, a position indicator can be included on the sensor head to allow the user to indicate the current position, or to advance the current position according to a specific sensor position sequence.

With respect to extensions and applications of the invention, computer-assisted auscultation could be applied to other anatomical sites, such as the carotid arteries or other arteries, and used to evaluate other sound types, such as pulmonary and gastrointestinal, with respect to different corresponding disease categories.

The invention could be applied to the evaluation of the status of artificial heart valves and for assessment of the associated thrombolytic risk. The invention could be applied to other animals, such as those encountered in veterinary practice.

Other users could find use for the invention, such as dentists deciding whether to prescribe prophylactic antibiotics, less highly trained medical personnel involved in cardiovascular screening, such as medics screening inductees for military service, or nurses conducting preparticipation screening for high school/college sports.

The invention could also be used in routine screening of critical personnel, such as pilots, public transit drivers, police and emergency first responder personnel.

Figure 2:
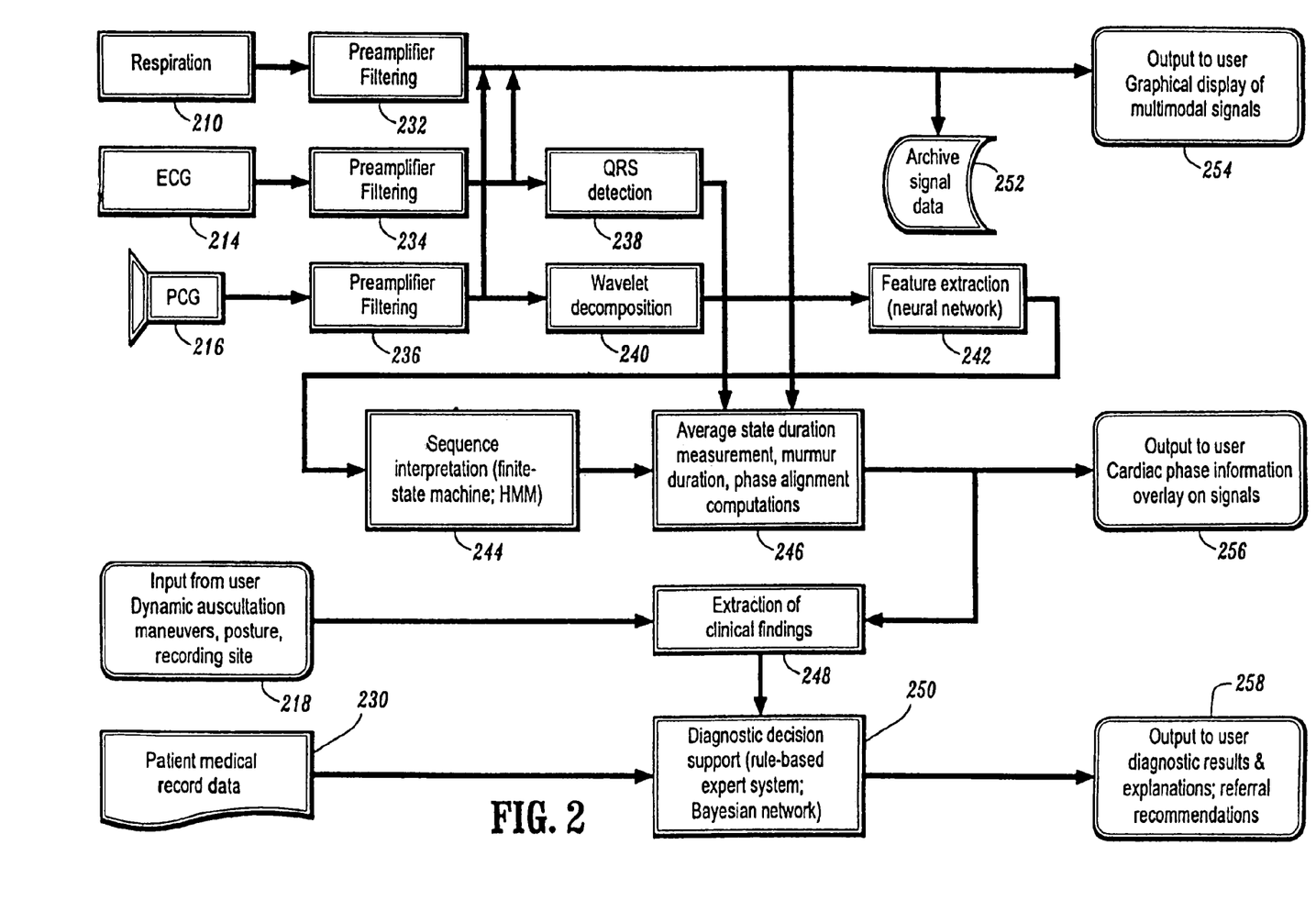
FIG. 2 is a high level block diagram illustrating a multi-modal cardiac diagnostic decision support system/method, according to an illustrative embodiment of the invention.

FIG. 2 is a high level block diagram illustrating a multi-modal cardiac diagnostic decision support system/method, according to an illustrative embodiment of the invention.

A respiration sensor 210 may optionally be employed to record a respiration signal. The respiration signal can be used to provide information about the respiratory activity of the patient for use in the interpretation of the cardiac acoustic signal. The respiratory signal can be obtained from, for example, an impedance respiration sensor or a nasal thermistor sensor.

An electrocardiogram (ECG) sensor 214 may optionally be employed to record the surface electrocardiogram to provide a reference signal for synchronizing the recorded acoustic signal. The recorded ECG need only comprise a single channel, requiring a single electrode and electrical reference.

A PCG sensor 216 may be used to record the cardiac acoustic waveform on the chest surface. The PCG sensor 216 should have a high signal to noise ratio, good immunity to ambient noise and motion artifact, and excellent low-frequency response, to as low as 1 Hz. The surface cardiac acoustic signal is preamplified, and digitized for signal processing and interpretation. One sensor for this purpose utilizes a fluid interface between the sensing element (a piezoelectric accelerometer) and the chest surface to achieve good impedance matching and much improved SNR. This sensor is described by Barnes et al., in "Improved Phono-cardiogram System Based on Acoustic Impedance Matching", Am. J. Physiol., 238(4):H604-9, April 1980.

Dynamic input 218 corresponding to the patient is received. Information about the patient's posture, site of PCG recording, along with any dynamic auscultation maneuvers associated with the signals being acquired at the time is input to the system using either a hand-held device that incorporates positional indicators, buttons and actuators or a combination of keyboard and mouse actions from a PC.

Patient Medical Data input 230 is also received. Medical information about the patient, including symptoms, history and results of physical examination, are entered into the diagnostic system in electronically readable form from a Smart card or other computer-based data source.

A respiration preamp & filter 232 is employed to amplify and filter the respiration using standard methods, to, e.g., increase the signal to noise ratio.

An ECG Preamp & Filter 234 is employed to amplify and filter the ECG signal using standard methods to, e.g., increase the signal to noise ratio.

A PCG Preamp & Filter 236 is employed to amplify and filter the PCG signal using standard methods to, e.g., increase the signal to noise ratio.

A QRS detection circuit 238 is employed to detect the QRS event in the ECG signal using standard methods. The output of the QRS detection circuit 238 provides synchronization information for the interpretation of the phonocardiogram.

A wavelet decomposition circuit 240 is employed to analyze the filtered signal using a wavelet decomposition to extract time-frequency information. The kernel function of the wavelet decomposition is not critical to the invention and, thus, any kernel function may be used while maintaining the spirit and scope of the invention. In a preferred embodiment of the invention, the wavelet employed is a Morlet wavelet. The wavelet decomposition is preferably scaled to compensate for variations in amplitude.

Neural network feature extractors 242 are trained from labeled examples to identify basic heart sounds, clicks and murmurs. In a preferred embodiment, the neural networks are of the time-delay variety, where the input span, number of layers, unit function, connectivity and initial weight selection are appropriately chosen according to well-known methods. However, it is to be appreciated that other types of neural networks may be used in accordance with the invention, while maintaining the spirit and scope thereof.

A sequence interpreter 244 interprets or parses the extracted features with reference to a state-transition model of the heart to determine the most probable sequence of cardiac events. The state machine can be probabilistic, such as, for example, a hidden Markov model. However, other types of state transition models may be used which maintain the spirit and scope of the invention.

A duration & phase measurement circuit 246 computes the average state durations of the sequence model. Event sequences are read off from the state trajectory of the sequence model.

A clinical findings extractor 248 extracts clinical findings from the acoustic signal based on the state duration, phase and amplitude information, along with dynamic and positional information provided by the user. Any heart murmurs present are quantified relative to the systolic/diastolic interval, and the murmurs are labeled with reference to the phase as early-, mid-, late- or pan-systolic or diastolic. The murmur intensity is scaled by a psychoacoustic measure and graded I through VI.

A decision support circuit 250 combines clinical findings with patient medical data input to produce estimates of the posterior probabilities of the covered cardiac diseases. This involves Bayesian networks and expert systems. Dynamic Bayesian networks can be used to model the progress of disease states.

An archive signal data store 252 archives recorded signals for later reference and display use. Preferably, the store 252 is an electronic or optical storage medium.

A signal output device 254 presents the recorded signals to the user. The signal output device 254 may be, for example, a display device (e.g., PC monitor, hand-held LCD, etc.) or printer. The output waveforms are identified and scaled according to factors selectable by the user.

An analysis-output device 256 provides the results of the analysis of the acoustic signal to the user. The analysis output device 256 may be, for example, a display device (e.g., computer monitor, hand-held LCD, etc.) or printer. The analysis output may be in graphical form, and may be overlaid on the signal output (waveform data). systolic and diastolic phase, and heart murmurs may be highlighted using an intuitive color-coded scheme.

A diagnostic output device 258 provides the results of the diagnostic decision support analysis to the user. The diagnostic output device 258 may be, for example, a display device (e.g., computer monitor, hand-held LCD, etc.) or printer. The diagnostic output may be in text form, and may include explanatory information and references to graphically displayed data. Most informative next tests or procedures are identified. The level of explanatory detail is selectable by the user.

Figure 3:
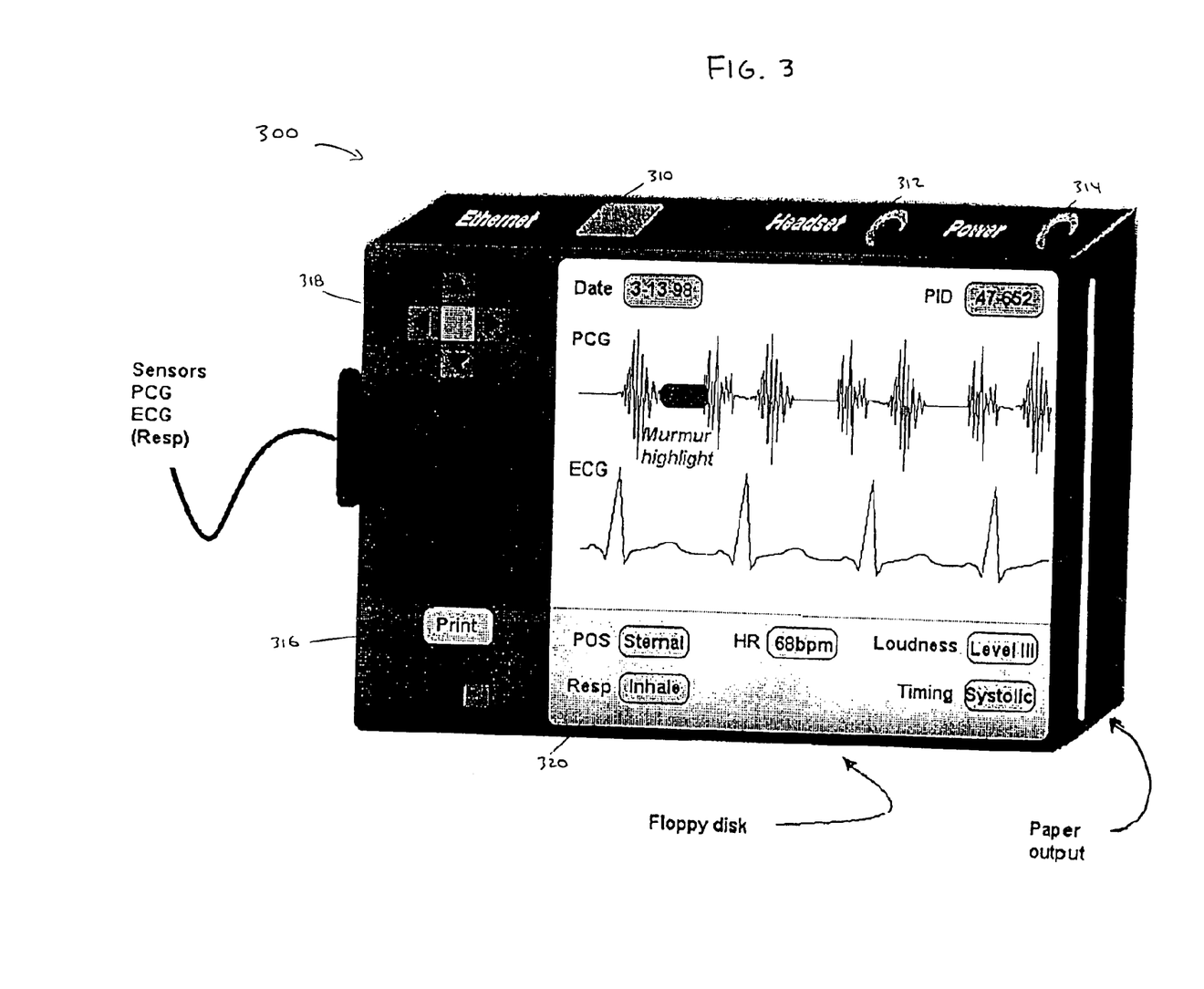
FIG. 3 is a diagram illustrating a portable cardiac diagnostic decision support system 300, according to an illustrative embodiment of the invention.

FIG. 3 is a diagram illustrating a portable cardiac diagnostic decision support system 300, according to an illustrative embodiment of the invention. The system 300 contains an Ethernet interface 310, a headset jack 312, a power switch 314, a print button 316, and a direction keypad 318. On a display 320 of the system 300 is shown the date, patient ID, PCG signal, ECG signal, POS, respiration state, heart rate, loudness setting, and cardiac timing. The system 300 includes a floppy drive for receiving a floppy disk, and a printer with paper output.

Figure 4:
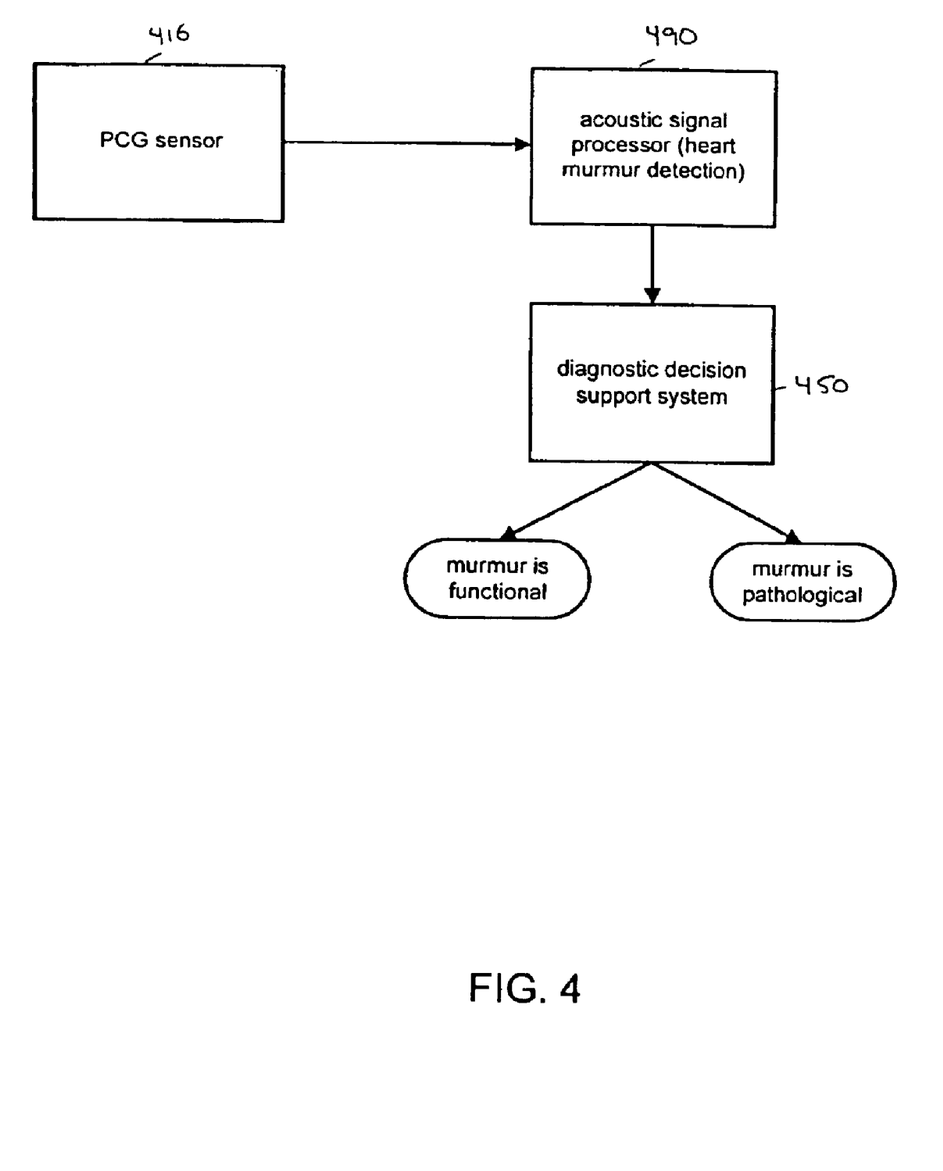
FIG. 4 is a high level block diagram illustrating a system/method for determining a status of heart murmurs, according to an illustrative embodiment of the invention.

FIG. 4 is a high level block diagram illustrating a system/method for determining a status of heart murmurs, according to an illustrative embodiment of the invention. A PCG sensor 416 obtains the cardiac acoustic waveform on the chest surface. An acoustic signal processor 490 detects a murmur, if any, from the cardiac acoustic signal. A diagnostic decision support system 450 determines whether the murmur is functional or pathological, based upon expert rules.

A description of some of the various novel elements of the invention will now be given. One such novel element is the use of neural networks for extraction of physiologically significant features from the processed cardiac acoustic signal; these features correspond to basic heart sounds, such as S1, or their components, such as M1, T1, murmurs, and so forth. Another novel element of the invention is the combination of wavelet processing of the phonocardiogram with neural network feature extraction. A further novel element of the invention is the processing of a feature string by a probabilistic finite-state automation to parse the cardiac acoustic signal to determine a most probable sequence of cardiac events given the cardiac acoustic signal. Yet another novel element of the invention is the extraction of clinical findings from the interpreted (parsed) cardiac acoustic signal, such as those employed in expert auscultation of the heart, including intensity, intensity profile, duration, time-alignment, sequence and spectral quality features, and so forth. Moreover, another novel element of the invention is diagnostic decision support using Bayesian networks in which the probability of cardiac diseases being present given the evidence of clinical findings derived from the results of signal processing and data from the patient medical record.

Additionally, another novel element of the invention is the determination of whether a detected murmur is functional or pathological on the basis of expert rules. Also, another novel element of the invention is the application of diagnostic decision support to the referral decision for echocardiography.

A description of some of the numerous advantages of the invention over manual auscultation of the heart will now be given. Using a specially designed sensor, the invention acquires a cardiac acoustic signal with much greater fidelity and at higher signal amplitude than is possible with the standard stethoscope. The signal acquisition and processing system is sensitive to broader range of frequencies than the unassisted human listener. The device is sensitive to frequencies outside the range of human hearing which contain significant diagnostic information for the evaluation of cardiac status and the diagnosis of cardiac disease. The invention is able to synchronize heart sounds with the diastolic/systolic phases of the heart, even under circumstances such as elevated heart rate, which make this task difficult for human listeners.

The invention provides an objective measure of murmur intensity that can be normalized to compensate for human psychoacoustics. The invention provides an objective measure of murmur duration, murmur frequency content, murmur phase and intensity profile. The invention interprets the sequence of heart sounds probabilistically using a statistical model of heart sound generation. Using digital signal processing techniques, the invention can distinguish the identity and sequence of brief heart sounds that are separated by short time durations.

The invention extracts clinical findings from a cardiac acoustic signal using adaptive nonlinear methods. The invention integrates statistical signal processing with probabilistic reasoning in a unified model (Bayesian network). The probabilistic reasoning model supports explanation of diagnostic recommendations. The invention provides documentation of the cardiac acoustic signal and its interpretation, in the form of an archival record of the signal, the analysis of the signal, and the interpretation of signal in the context of the patient medical record data. The signal acquisition, processing and interpretation provides support and rationalization for the decision to refer for more expensive diagnostic tests, typically diagnostic imaging such as ultrasound.

Although the illustrative embodiments have been described herein with reference to the accompanying drawings, it is to be understood that the present system and method is not limited to those precise embodiments, and that various other changes and modifications may be affected therein by one skilled in the art without departing from the scope or spirit of the invention. All such changes and modifications are intended to be included within the scope of the invention as defined by the appended claims.

What is claimed is:

1. A method for extracting features from cardiac acoustic signals, comprising the steps of:
   obtaining a cardiac acoustic signal;
   computing a wavelet representation of the acoustic signal; and
   extracting physiologically significant features from the cardiac acoustic signal, using a time delay neural network to process the wavelet representation.

2. The method according to claim 1, wherein the physiologically significant features correspond to at least one of basic heart sounds and components of the basic heart sounds.

3. A method for evaluating cardiac acoustic signals, comprising the steps of:
- obtaining a cardiac acoustic signal;
- obtaining a respiration signal;
- analyzing the cardiac acoustic signal with a wavelet decomposition to extract time-frequency information;
- identifying basic heart sounds using time delay neural networks applied to the extracted time-frequency information; and
- interpreting the cardiac acoustic signal using the identified heart sounds and the respiration signal.

4. A program storage device readable by a machine, tangibly embodying a program of instructions executable by the machine to perform method steps for determining cardiac event sequences from cardiac acoustic signals, the method steps comprising:
- obtaining a cardiac acoustic signal; and
- processing a sequence of features extracted from the cardiac acoustic signal by a probabilistic finite-state automaton to determine a most probable sequence of cardiac events given the cardiac acoustic signal.

5. The program storage device according to claim 4, wherein the probabilistic finite-state automaton is a hidden markov model.

6. The program storage device according to claim 4, wherein the step of processing a sequence of features extracted from the cardiac acoustic signal further includes:
- computing a wavelet representation of the acoustic signal; and
- extracting the features from the cardiac acoustic signal, using a neural network to process the wavelet representation.

7. The program storage device according to claim 4, further comprising instructions for performing the step of extracting a plurality of clinical findings from the sequence of cardiac events.

8. The program storage device according to claim 7, further comprising Instructions for performing the step of determining whether to refer the patient for echocardiography, based upon the extracted clinical findings.

9. The program storage device according to claim 7, further comprising instructions for performing the step of determining whether to refer the patient for further treatment by a cardiac specialist, based upon the extracted clinical findings.

10. The program storage device according to claim 7, wherein the clinical findings correspond to finds which are typically derived from auscultation of a heart.

11. The program storage device according to claim 7, wherein the clinical findings correspond to basic heart sounds and murmurs.

12. The program storage device according to claim 11, wherein the clinical findings comprise at least one of present intensity, intensity profile, duration, time-alignment, and sequence and spectral quality features.

13. A program storage device readable by a machine, tangibly embodying a program of Instructions executable by the machine to perform method steps for determining a status of heart murmurs, the method steps comprising:
- obtaining a cardiac acoustic signal;
- detecting a murmur, if any, from the cardiac acoustic signal by processing a sequence of features extracted from the cardiac acoustic signal by probabilistic finite-state automaton to determine a most probable sequence of cardiac events given the cardiac acoustic signal; and
- determining whether the murmur is one of functional and pathological, based upon expert rules.

14. A system for extracting features from cardiac acoustic signals, comprising:
- a sensor adapted to obtain a cardiac acoustic signal;
- means for computing a wavelet representation of the acoustic signal; and
- a time delay neural network adapted to process the wavelet representation extract physiologically significant features from the cardiac acoustic signal.

15. The system according to claim 14, wherein the physiologically significant features correspond to at least one of basic heart sounds and components of the basic heart sounds.

16. A system for evaluating cardiac acoustic signals, comprising:
- a sensor adapted to obtain a cardiac acoustic signal;
- a respiration sensor adapted to obtain a respiration signal;
- a wavelet decomposition circuit adapted to analyze the cardiac acoustic signal to extract time-frequency information;
- a time delay neural network adapted to identify basic heart sounds from the extracted time-frequency information; and
- evaluating means for interpreting the cardiac acoustic signal using the identified heart sounds and the respiration signal.

17. A system for determining a status of heart murmurs, comprising:
- a sensor adapted to obtain a cardiac acoustic signal;
- an acoustic signal processor adapted to detect a murmur, if any, from the cardiac acoustic signal by processing a sequence of features extracted from the cardiac acoustic signal using probabilistic finite-state automaton to determine a most probable sequence of cardiac events given the cardiac acoustic signal; and
- means for determining whether the murmur is one of functional and pathological, based upon expert rules.

18. A program storage device readable by a machine, tangibly embodying a program of instructions executable by the machine to perform method steps for extracting features from cardiac acoustic signals, the method steps comprising:
- obtaining a cardiac acoustic signal;
- computing a wavelet representation of the acoustic signal; and
- extracting physiologically significant features from the cardiac acoustic signal, using a time delay neural network to process the wavelet representation.

19. The program storage device according to claim 18, wherein the physiologically significant features correspond to at least one of basic heart sounds and components of the basic hear sounds.

20. A program storage device readable by a machine, tangibly embodying a program of instructions executable by the machine to perform method steps for evaluating cardiac acoustic signals, the method steps comprising:
- obtaining a cardiac acoustic signal;
- obtaining a respiration signal;
- analyzing the cardiac acoustic signal with a wavelet decomposition to extract time-frequency information;
- identifying basic heart sounds using time delay neural networks applied to the extracted time-frequency information; and
- interpreting the cardiac acoustic signal using the identified heart sounds and the respiration signal.

21. A method for extracting features from cardiac acoustic signals, comprising the steps of:
   obtaining a cardiac acoustic signal;
   computing a wavelet representation of the acoustic signal;
   extracting physiologically significant features from the cardiac acoustic signal, using a neural network to process the wavelet representation; and
   processing the physiologically significant features extracted from the cardiac acoustic signal using a probabilistic finite-state automaton to determine a most probable sequence of cardiac events represented by the cardiac acoustic signal.

* * * * *